(12) United States Patent
Lang

(10) Patent No.: US 6,712,072 B1
(45) Date of Patent: Mar. 30, 2004

(54) RESPIRATOR MASK

(75) Inventor: Bernd Christoph Lang, Gauting (DE)

(73) Assignee: MAP Medizintechnik fur Arzt und Patient GmbH & Co. KG (DE)

( * ) Notice: Subject to any disclaimer, the term of this patent is extended or adjusted under 35 U.S.C. 154(b) by 0 days.

(21) Appl. No.: 09/622,983

(22) PCT Filed: Feb. 25, 1999

(86) PCT No.: PCT/EP99/01218
§ 371 (c)(1),
(2), (4) Date: Aug. 25, 2000

(87) PCT Pub. No.: WO99/43375
PCT Pub. Date: Sep. 2, 1999

(30) Foreign Application Priority Data

Feb. 25, 1998 (DE) .......................... 198 07 961

(51) Int. Cl.[7] .............................................. A62B 18/08
(52) U.S. Cl. ............................. 128/206.27; 128/207.11; 128/206.16; 128/207.13
(58) Field of Search ....................... 128/204.18, 206.23, 128/206.24, 206.26, 206.27, 206.16, 206.28, 207.11, 207.13

(56) References Cited

U.S. PATENT DOCUMENTS

| | | | |
|---|---|---|---|
| 4,201,205 A | 5/1980 | Bartholomew | 128/205.25 |
| 5,094,236 A | * 3/1992 | Tayebi | 128/206.12 |
| 5,538,014 A | * 7/1996 | Wilson et al. | 128/863 |
| 5,560,354 A | * 10/1996 | Berthon-Jones et al. | 128/205.25 |
| 6,092,521 A | * 7/2000 | Miura | 128/201.13 |

FOREIGN PATENT DOCUMENTS

| | | | | |
|---|---|---|---|---|
| DE | 19548380 | * | 7/1996 | |
| EP | 462701 A1 | | 12/1991 | A61M/16/06 |
| FR | 522485 | | 3/1921 | |
| GB | 1315893 | | 5/1973 | B21D/26/04 |
| GB | 2275614 | * | 9/1994 | |
| WO | WO 96/28207 | | 9/1996 | A61M/16/00 |

* cited by examiner

*Primary Examiner*—Aaron J. Lewis
*Assistant Examiner*—Mital Patel
(74) *Attorney, Agent, or Firm*—Ohlandt, Greeley, Ruggiero & Perle, LLP; George W. Rauchfuss, Jr.

(57) ABSTRACT

The invention relates to a respirator mask which can be repeatedly fitted to different facial shapes. It consists of a mask base body and a support structure which supports the mask base body and can repeatedly be deformed plastically above a specific limit temperature so that the respirator mask can be fitted to different facial shapes.

14 Claims, 2 Drawing Sheets

RESPIRATOR MASK

Figure 1:
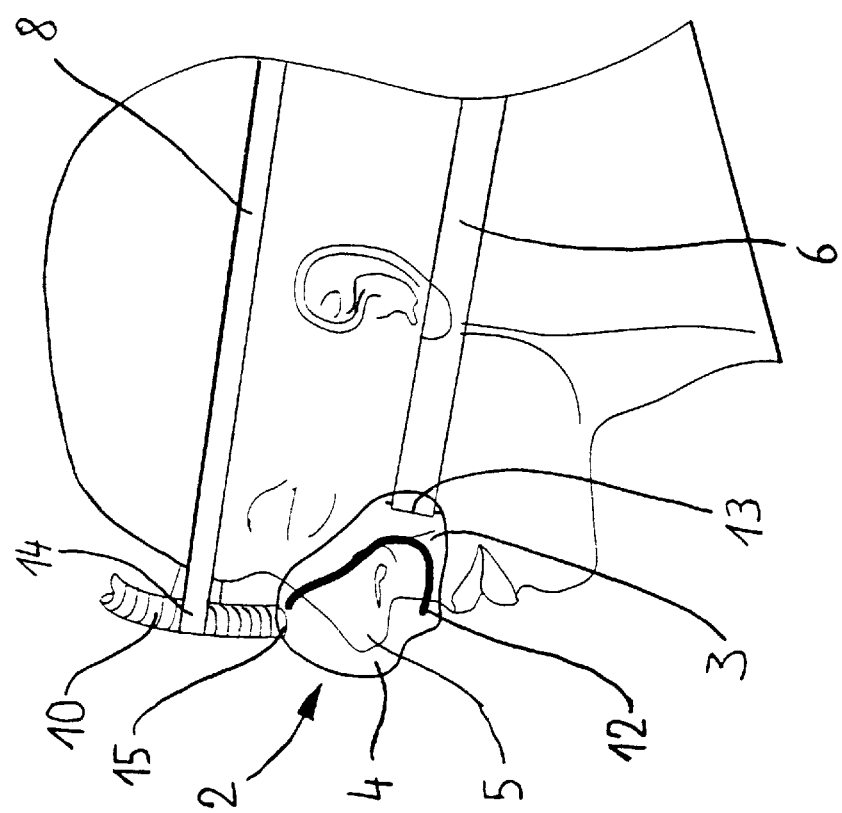

The present invention relates to a respirator mask which can be repeatedly fitted to different facial shapes.

In general, conventional respirator masks consist of a mask part which is placed over the nose and/or mouth of a patient to be supplied with air, a respirator tube for supplying respiration air and/or for carrying away exhaled air, and attachment means for attaching the respirator mask to a patient. The mask part itself has a relatively flexible edge area, which can be pressed by a corresponding contact pressure to the facial shape of a patient, and a center area, which is relatively stiff as compared to this edge area and at which, for example, the respirator tube as well as attachment straps are attached.

Conventional respirator masks of this kind have particularly the disadvantage that for achieving a good fit and for sealing the edge area of the mask at the face of a patient to be supplied with air, a relatively large contact pressure is required, and when wearing the mask the patient may possibly suffer from complaints such as headache, pain caused by pressure or wounds. A further disadvantage of the conventional respirator mask lies in the fact that it has to be manufactured from different materials so that, on the one hand, the supporting center area and, on the other hand, the flexible edge area can be realized. Moreover, it is difficult with conventional respirator masks to fit the mask to different head sizes because due to the stiff center area of the mask part a specific shape and size of the nose and/or mouth part is already given, so that the edge area possibly no longer fits completely to the face of the patient even when a considerable contact pressure is applied.

DE-A-195 48 380 relates to a respirator mask comprising an essentially shell-shaped, dimensionally stable base body on which a connection knee or element, a bracket with a spacing cushion and a connection mask are provided. The connection mask is the part of the respirator mask which comes in contact with the face of the patient. At least at the edge area of a breaking-through for the nose of a patient to be supplied with air, the connection mask is formed of a material which can be deformed plastically if a temperature higher than room temperature is applied and which is stiff at a lower temperature.

It is the object of the present invention to provide an improved respirator mask. This object is achieved with the features of the claims.

In achieving this object, the invention starts out from the basic idea that at least the edge area of the respirator mask, which can be placed over the nose and/or mouth of a patient, consists of a deformable material which is supported by a supporting structure (supporting frame or supporting element) which is stiff at normal ambient temperatures but can, however, be deformed plastically when the temperature increases. Thus, the shape relevant for fitting the respirator mask to the facial shape of the patient can be changed repeatedly at an increased temperature so that the respirator mask can be fitted to the different facial shapes of the patients.

It is particularly advantageous in the respirator mask of the present invention that the mask can repeatedly be deformed plastically to -fit it to different facial shapes, that the wearing comfort is increased, i.e. that an improved fit and, at the same time, a lower contact pressure is guaranteed, that the mask can alternatively consist of only one material for the entire mask base body or of different materials, e.g. for the center area and the edge area, and that it can be manufactured and disposed of at low cost.

Figure 2:
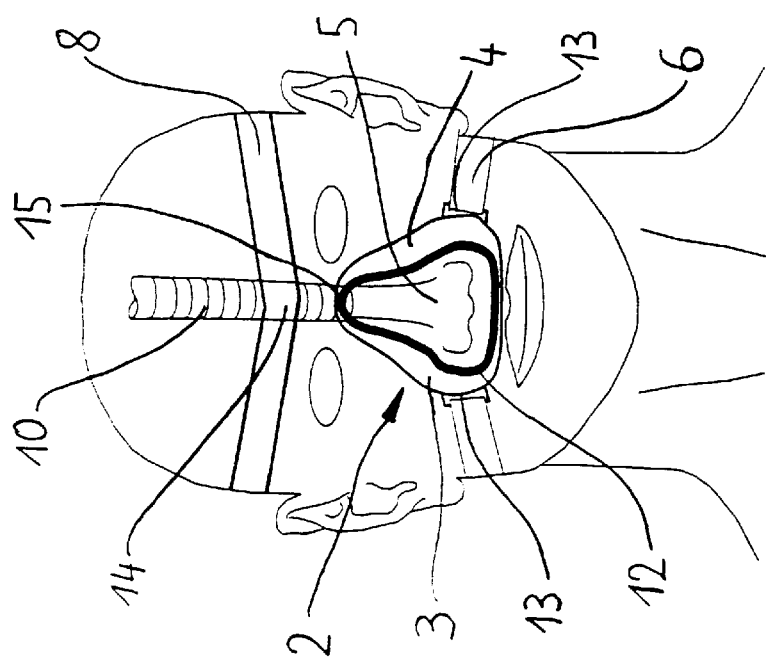
Figure 4:
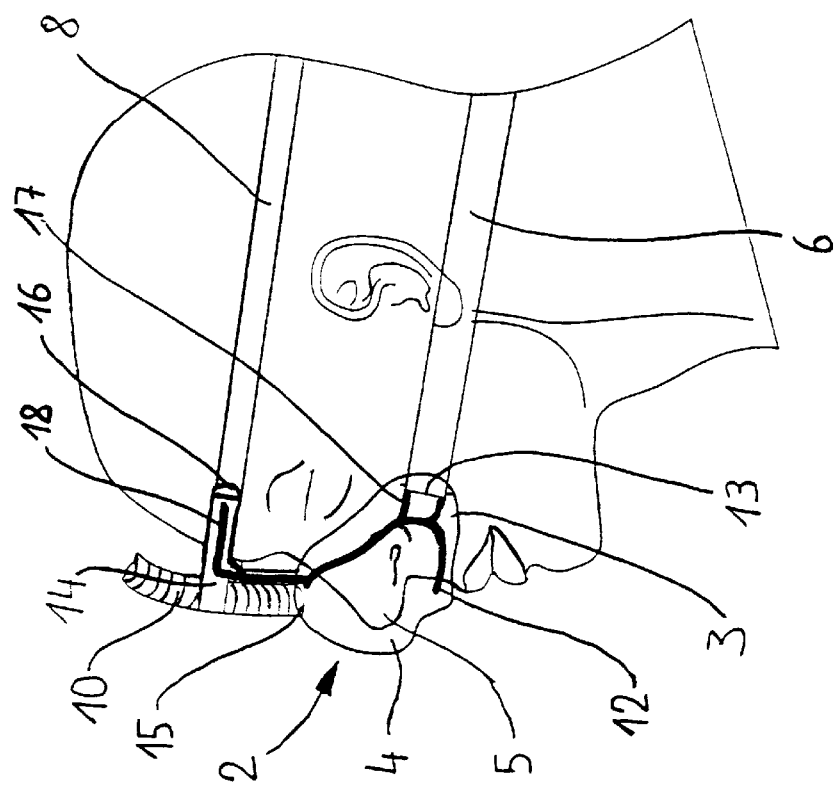
Figure 3:
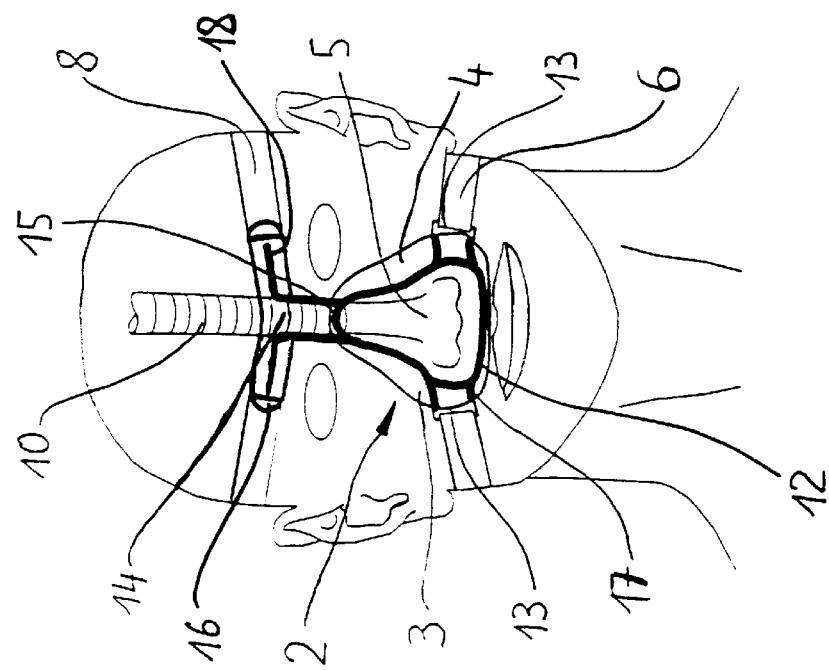

In the following, the invention will be discussed exemplarily on the basis of preferred embodiments. The drawings show in:

FIG. 1 a first embodiment of the respirator mask of the present invention on the patient in a front view;

FIG. 2 a side view of FIG. 1;

FIG. 3 a second embodiment of the respirator mask of the present invention on the patient in a front view; and FIG. 4 a side view of FIG. 3.

The respirator mask 2 as shown in FIGS. 1 and 2 comprises a mask base body 4 which can be placed over the nose and/or mouth of a patient and which can be attached at the head of the patient by means of attachment means 6 and 8, for instance elastic straps. The mask base body 4 consists preferably of a well-deformable edge area 3 and a center area 5 being relatively stiff as compared to said edge area 3. Moreover, preferably in its center area 5, the mask base body 4 is connected to a respirator tube 10 which is connected with a respirator means (not shown) in order to supply the patient with respiration air and/or to carry exhaled air away from the patient.

The mask base body 4, in particular the edge area 3 of the respirator mask 2, consists of a material which is well tolerated by the skin and can be cleaned easily, preferably of a single material, in particular a plastics material such as, for example, silicone or polyurethane, i.e. the center area 5 and the edge area 3 preferably consist of the same material having, however, a different strength (hardness) and/or material thickness.

The respirator mask 2 furthermore comprises a support structure 12 which supports the mask base body 4 and/or the edge area 3 and can be located in the inside of, at the outside of, or in the mask base body 4. Preferably, the support structure 12 is, as shown in FIGS. 1 and 2, shaped as a support frame and formed in the edge area 3 of the respirator mask 2, but can, however, also be realized in the form of a plurality of support elements or a combination of support frame and support elements. Moreover, it is also possible to provide instead of the support frame or in addition thereto a shell-shaped, i.e. three-dimensional support element (not shown) preferably in the area of or around the nose of the patient. This further increases the stability of the respirator mask of the present invention, in particular the stability of the support structure 12.

The support structure 12 preferably consists of a material which can repeatedly be deformed plastically at relatively low temperatures, e.g. 70° C., and which is relatively stiff at use temperature, e.g. below 40° C., and fulfils the support function in this state. Suitable materials for the support structure are, for example, Bi alloys, BiCd alloys as well as in alloys, heat-deformable plastics materials and/or waxes having a suitably defined softening point or range. Thus, for instance by a suitable selection of the composition of the alloy, the plastics material or the wax, the physical parameters such as melting temperature, softening range and mechanical properties of the material for the support structure 12 can be adjusted.

For fitting the respirator mask 2 to the facial shape of a patient, the mask base body 4 together with the support structure 12 is heated up to at least the above mentioned limit temperature, for instance by putting it into a suitably heated water bath, so that the support structure 12 can be deformed plastically without a considerable force being necessary. Subsequently, the respirator mask 2 is preferably cooled down quickly, so that the mask base body 4 has a temperature tolerable by the patient while the support structure 12 is still plastically deformable. By now placing the respirator mask 2 at the face of the patient, the support structure 12 and the edge area 3 can be fitted and/or fit themselves automatically to the facial shape. The shell of the support structure 12 is realized such that the heat generated during hardening is preferably carried away from the patient, i.e. the support structure 12 lies preferably close to the surface of the respirator mask 2 facing away from the patient. After also the support structure 12 has cooled down, also the edge area 3 of the respirator mask 2 maintains the shape which was individually fitted to the facial shape of the patient. This process can be repeated as often as required for any desired facial shape.

A second embodiment of the respirator mask 2 of the present invention is shown in FIGS. 3 and 4. This embodiment essentially corresponds to the embodiment described above, wherein equal elements have equal reference signs.

The respirator mask 2 as shown in FIGS. 3 and 4 differs from that described in FIGS. 1 and 2 essentially in that also support structures 17 for attachment points 13 of the attachment means 6 and 8 and/or support structures 18 for a mask fixing point 14 and/or a respirator tube connection point 15 are provided in the mask base body 4, which have essentially the same properties as the support structure 12 described above. By means of such support structures for the attachment means 13, 14 and/or 15, the fit of the mask 2 can further be improved individually for the patients.

For this purpose, the mask base body 4 can preferably extend to the mask fixing point 14 and/or at least partially in the direction of the attachment means 8. Moreover, the support structure 18 can also comprise a base body corresponding to the mask base body and being connected with the mask base body 4. In these cases it can be advantageous to provide attachment elements 16 for the attachment means 8 in the portion of the base body 4 extending in the area of the support structure 18.

What is claimed is:

1. A respirator mask (2) comprising a base mask body (4) which is formed of an essentialy flexible material and can be fitted flexibly to different facial shapes and an integrated support structure (12, 17, 18) which supports the mask base body (4) and which can repeatedly be deformed plastically above a specific limit temperature whereby deformation of the support structure results in a deformation of the mask base body (4) in order to fit said respirator mask (2) repeatedly to different facial shapes, and wherein said limit temperature is between 40° C. and 120° C.

2. The respirator mask (2) according to claim 1, wherein said mask base body (4) consists of a deformable edge area (3) and a center area (5) with the center area (5) being stiff as compared to the deformable edge area (3), and wherein said support structure (12) supports said edge area (3).

3. The respirator mask (2) according to claim 2, further comprising attachment means (6, 8) for attaching the mask to a patient and a respirator tube (10) for at least one of:
    providing respirator air, or
    carrying away exhaled air.

4. The respirator mask (2) according to claim 3, wherein said mask base body (4) comprises at least one of:
    at least one further support structure (17) for attachment points (13) of said attachment means (6, 8), or
    at least one further support structure (18) at a mask fixing point (14) in the area of at least one of:
    a forehead of the patient or
    at a respirator tube connection point (15).

5. The respirator mask (2) according to claim 4, wherein said at least one further support structure can repeatedly be deformed plastically above a specific temperature.

6. The respirator mask (2) according to claim 4, wherein said support structure (12) extends into at least one of:
    an area of a mask fixing point (14) at the forehead of the patient, or an area of attachment points (13) of said attachment means (6, 8).

7. The respirator mask (2) according to claim 1 wherein at least said edge area (3) of said mask base body (4) consists of a material which is repeatedly deformable, well tolerated by the skin and can be cleaned easily.

8. The respirator mask (2) according to claim 7, wherein the material is silicone or polyurethane.

9. The respirator mask (2) according to claim 1 wherein said support structure (12) is formed of at least one of: a metal alloy, a heat-deformable plastics material or a wax.

10. The respirator mask (2) according to claim 1 wherein the limit temperature is 70° C.

11. The respirator mask (2) according to claim 1 wherein said support structure (12) is relatively close to a surface of said mask base body (4) facing away from the patient.

12. The respirator mask (2) according to claim 1, wherein said support structure (12) is shell-shaped.

13. The respirator mask (2) according to claim 12, wherein the shell-shape is provided in the area around the nose of the patient.

14. A respirator mask (2) comprising a base mask body (4) which is formed of an essentialy flexible material and can be fitted flexibly to different facial shapes and an integrated support structure (12, 17, 18) which supports the mask base body (4) and which can repeatedly be deformed plastically above a specific limit temperature in order to fit said respirator mask (2) repeatedly to different facial shapes, wherein said support structure is formed of a metal alloy and the metal alloy is a Bi, BiCd or In alloy.

* * * * *